United States Patent
Fukaya et al.

[11] Patent Number: 6,065,327
[45] Date of Patent: May 23, 2000

[54] AIR FUEL RATIO SENSOR WITH EXTERNALLY LOCATED HEAT SOURCE

[75] Inventors: Kenji Fukaya, Chiryu; Masanobu Yamauchi, Kariya, both of Japan

[73] Assignee: Denso Corporation, Japan

[21] Appl. No.: 09/207,654

[22] Filed: Dec. 9, 1998

[30] Foreign Application Priority Data

Mar. 31, 1998 [JP] Japan .................................. 10-105811

[51] Int. Cl.[7] .................................................... G01N 7/00
[52] U.S. Cl. ........................ 73/23.32; 73/23.32; 422/90
[58] Field of Search .............................. 73/23.31, 23.32; 422/90, 91, 94; 204/429

[56] References Cited

U.S. PATENT DOCUMENTS 4,512,871  4/1985  Kato et al. .

FOREIGN PATENT DOCUMENTS 63-83648  of 0000  Japan .

Primary Examiner—Hezron Williams
Assistant Examiner—Jay L. Politzer
Attorney, Agent, or Firm—Nixon & Vanderhye PC

[57] ABSTRACT

An air fuel ratio sensor having an externally located heat source and an optical fiber heat introduction member. The heat introduction member is inserted into an inside chamber of a sensor element having a U-shaped cross section, and is connected to the external heat source outside the sensor element for introducing heat from the external heat source into the inside chamber. The heat introduction member is further connected to a temperature detector outside the sensor body. Accordingly, an air fuel ratio sensor can have sufficient durability and sufficient starting performance, and a temperature inside the sensor element can be readily detected.

7 Claims, 1 Drawing Sheet

|  | 100W | 150W | 300W |
|---|---|---|---|
| INCIDENT FACE TEMPERATURE (°C) | 285 | 398 | 716 |
| OUTGOING FACE TEMPERATURE (°C) | 103 | 206 | 491 |
| OUTER CIRCUMFERENCE FACE TEMPERATURE (°C) | 55 | 72 | 128 |
| CARRY-OVER PERIOD (sec.) | 12 | 8 | 5 |

AIR FUEL RATIO SENSOR WITH EXTERNALLY LOCATED HEAT SOURCE

CROSS REFERENCE TO RELATED APPLICATION

This application is based upon and claims the benefit of priority of Japanese Patent Application No. 10-105811, filed on Mar. 31, 1998, the contents of which are incorporated herein by reference.

BACKGROUND OF THE INVENTION

1. Field of the Invention

This invention relates to generally to motor vehicle sensors, and more particularly an air fuel ratio sensor used for controlling an air fuel ratio of an automotive engine or the like.

2. Description of the Related Art

Conventionally, an air fuel ratio sensor is disposed in an exhaust system of an automotive engine, and combustion of the automotive engine is controlled based on the air fuel ratio detected by the sensor. Accordingly, purification efficiency of exhaust gas in a three-way catalytic converter or the like, which is also disposed in the exhaust system, can be improved.

The air fuel ratio sensor typically has a sensor element having a U-shaped cross-section and an inside chamber formed therein into which atmospheric air is introduced as reference gas. The sensor element is accommodated in a housing, and the housing is covered with a measurement gas side cover at a lower side thereof and with an atmosphere side cover at an upper side thereof. A heater is disposed in the inside chamber of the sensor element to rapidly raise a temperature of the sensor element up to an activation temperature. The heater is composed of a conventional insulating ceramic member holding therein a heating member made of W, W-Re, W-Mo, Pt, or the like which generates heat upon receiving electricity.

This kind of ceramic heater is, however, easily damaged by vibrations, impact and the like, resulting in deterioration of mechanical durability of the air fuel ratio sensor. Further, heat resistance of the heating member material, such as W or Pt, is not so large that the heater can be used at a temperature more than 1000° C. for an extended period of time. Therefore, the temperature raising performance of the sensor element is low. As a result, so that the air fuel ratio sensor cannot exhibit a sufficient starting performance, meaning that the sensor is not capable of detecting the air fuel ratio immediately after the sensor element starts to be heated by the heater.

In addition, the temperature in the sensor element needs to be detected to ensure the durability, prevent damage, and improve sensor characteristics. However, the sensor element is so small that it is difficult for a temperature detector to be disposed in the inside chamber of the sensor element. This makes it difficult to detect the temperature in the sensor element when the air fuel ratio sensor is operated.

SUMMARY OF THE INVENTION

The present invention has been made in view of the above problems. An object of the present invention is to provide an air fuel ratio sensor having sufficient mechanical durability and sufficient starting performance, and being capable of readily detecting the temperature inside a sensor element thereof.

Briefly, according to the present invention, a heat (light) introduction member is disposed in an inside chamber of a sensor element, and is connected to an external heat source disposed outside the sensor element in order to introduce heat from the external heat source into the inside chamber. Accordingly, the temperature of the sensor element can be rapidly increased up to an element activation temperature, resulting in improved starting performance. Because the heat source is disposed outside the sensor element, the inside of the sensor element is not damaged by the heat from the heat source. Because the heat introduction member is not made of a ceramic material, the mechanical strength of the air fuel ratio sensor is improved, resulting in high durability of the air fuel ratio sensor.

When the external heat source emits light, the heat introduction member introduces the light into the inside chamber as thermal energy. Preferably, the heat introduction member is composed of a plurality of optical fibers. More preferably, the heat introduction member has an outgoing face at an end therof facing a bottom portion of the inside chamber so that the light is introduced into the chamber from the outgoing face.

The air fuel ratio sensor also has a temperature detector connected to the heat introduction member and disposed outside the sensor element for detecting the temperature in the inside chamber.

BRIEF DESCRIPTION OF THE DRAWINGS

Other objects and features of the present invention will become more readily apparent from a better understanding of the preferred embodiments described below with reference to the following drawings.

DETAILED DESCRIPTION OF THE PREFERRED EMBODIMENT

Figures 1, 2:
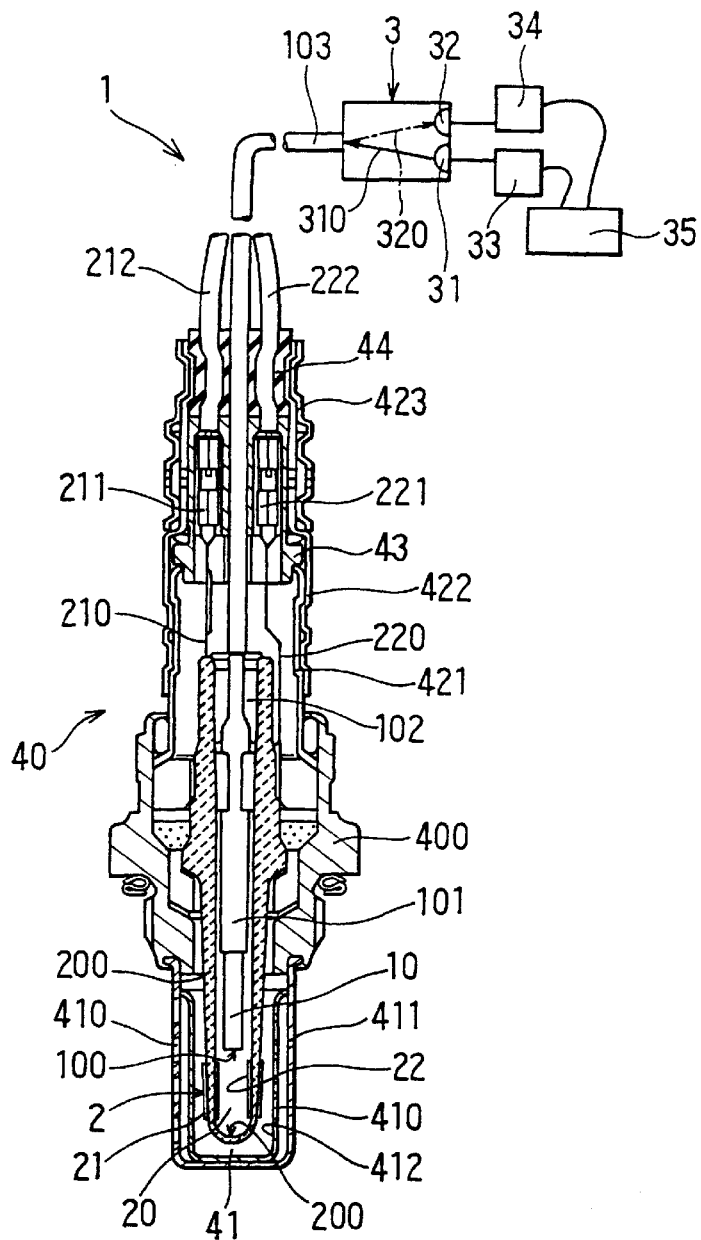
FIG. 1 is a cross-sectional view showing an air fuel ratio sensor including a heat introduction member in a preferred embodiment of the present invention.
FIG. 2 is a table showing characteristics of the heat introduction member of the air fuel ratio sensor in the embodiment.

Referring to FIG. 1, an air fuel ratio sensor in a preferred embodiment has a housing 400 and a sensor element fixedly inserted into the housing 400. A lower end of the housing 400 is covered with measurement gas side double cover 411, 412. The measurement gas side double cover 411, 412 defines therein a measurement gas chamber 41 and has several measurement gas introduction holes 410. Atmosphere side covers 421, 422, 423 are fixed to an upper end of the housing 400 by caulking. An insulator 43 and a rubber bushing 44 are disposed in the atmosphere side covers 421, 422, 423, and connecting terminals 211, 221 of the sensor element 2 and a heat introduction member 10 composed of optical fibers (described below) are inserted into the rubber bushing 44 and the insulator 43. The housing 400, the measurement gas side double cover 411, 412 and the atmosphere side covers 421, 422, 423 constitute a sensor body 40 of the air fuel ratio sensor 1.

The sensor element 2 is composed of a solid electrolyte body 200 having a U-shaped cross-section and oxygen ion conductivity, and an inside electrode 22 and an outside electrode 21 formed on inner and outer faces of the solid electrolyte body 200, respectively. The inside and outside electrodes 21, 22 are electrically connected to terminals 210, 220, and the terminals 210, 220 are electrically connected to lead wires 212, 222 via the connecting terminals 211, 221. Accordingly, a sensor output is taken out from the lead wires 212, 222.

The sensor element 2 defines an inside chamber 20 therein, and the heat introduction member 10 is fixed in the inside chamber 20 by a fixing member 102. The heat introduction member 10 is covered with a cover member 101 except in the vicinity of an open end 100 thereof that is open toward a bottom portion 200 of the inside chamber 20. The heat introduction member 10 extends through the insulator 43 and the rubber bushing 44 and protrudes outside of the sensor body 40. A rear end portion 103 of the heat introduction member 10 disposed outside the sensor body 40 is connected to a case 3. An external heat (light) source 31 such as a halogen lamp connected to a power source 33, and a light-intercepting element 32 connected to a temperature detector 34, are disposed in the case 3. A radiation thermometer constitutes the temperature detector 34 in this embodiment. A control unit 35 controls the power source 33 and the temperature detector 34.

Next, operation of the air fuel ratio sensor 1 will be described. First, the power source 33 is switched on by the control unit 35 so that the halogen lamp 31 is turned on. Light emitted by the halogen lamp 31 is transmitted to the open end 100 via the heat introduction member 10 and is projected onto the bottom portion 200 of the inside chamber 20 from the open end 100. Accordingly, the sensor element 2 is heated.

After that, the temperature inside the sensor element 2 is detected. Specifically, the power supply 33 is switched off by the control unit 35 so that the halogen lamp 31 is turned off. Then, the control unit 35 operates the temperature detector 34. The light radiated from the sensor element 2 in response to the temperature of the sensor element 2 is introduced into the case 3 via the heat introduction member 10, and is received by the light-intercepting element 32. Accordingly, the temperature detector 34 detects the temperature of the sensor element 2. In FIG. 1, the traces of the light in the case 3 are indicated by reference numerals 310, 320.

Characteristics of the air fuel ratio sensor 1 described above were examined by the following test. In the test, first, light power boxes, respectively corresponding to the case 3 and holding a halogen lamp, were prepared. The used halogen lamps had output powers of 100 W, 150 W, and 300 W, respectively. A bundle of optical fibers having a fiber diameter of 50 $\mu$m, a bundle diameter of 5 mm, and a length of 1000 mm, was connected to each of the boxes. Incidentally, the fiber diameter represents a diameter of one of the optical fibers for transmitting thermal energy, and the bundle diameter represents an outer diameter of the bundle.

Then, temperatures of the bundle of the optical fibers were measured by a thermocouple at an incident face for receiving the light emitted from the halogen lamp, an outgoing face from which the light was released outside after passing through the optical fibers, and an outer circumference face. The measurement was carried out at a room temperature of 28.1° C. Further, a carry-over period from the start of the heating to the time when the temperature of the incident face rose to 250° C. was measured. The results are shown in FIG. 2.

As understood from FIG. 2, it was confirmed that the temperature of the outgoing face of the optical fibers was increased by receiving the light emitted from the halogen lamps. It was further confirmed that the temperature of the outer circumference face of the optical fibers was not increased as largely as that of the outgoing face.

These results imply that, in the air fuel ratio sensor 1, the heat introduction member 10 introduces the light emitted from the halogen lamp as the external heat source 31 into the sensor element 2 so that the sensor element 2 is heated. The heat introduction member 10 minimally hardly heats parts except the inside of the sensor element 2.

Further, as understood from FIG. 2, the carry-over period until the incident face reaches the temperature of 250° C. is very short, i.e., shorter than several seconds. Accordingly, the sensor element 2 is heated up to an element activation temperature in a short period after the halogen lamp is turned on, so that the air fuel ratio sensor 1 detects the air fuel ratio. This implies that the air fuel ratio sensor 1 exhibits a sufficient starting performance.

The features and effects of the air fuel ratio sensor 1 will be briefly described below. In the air fuel ratio sensor 1, because the heat introduction member 10 is composed of optical fibers, preferably of multicomponent glass type, the mechanical strength of the air fuel ratio sensor 1 is superior compared to a conventional sensor having a ceramic heater.

Also, because the light from the external heat source 31 quickly heats the sensor element 2 up to the element activation temperature (see FIG. 2), sufficient sensor starting performance is achieved. Further, because the external heat source 31 is disposed outside the sensor body 40, the inside of the air fuel ratio sensor 1 is not damaged by the heat from the heat source 31.

In addition, because the heat introduction member 10 conducts radiation from inside the chamber 20 to outside the chamber 20 and because the light-intercepting element 32 and the temperature detector 34 cooperatively detect the radiation to measure the temperature inside the sensor element 2, the temperature inside the sensor element 2 can be readily measured. Because the heat introduction member 10 is composed of optical fibers, the thermal energy can be readily transmitted into the inside chamber or from the inside chamber at a high speed without producing large intermediate loss.

It is preferable for the heat introduction member 10 to be made of material having sufficient heat transmitting property so that the air fuel ratio sensor has a desirable starting performance. It is further preferable for the heat introduction member 10 to be made of material having high flexibility. Accordingly, ease of connecting the heat introduction member 10 to the external heat source and the sensor body is improved, and the air fuel ratio sensor can be more readily installed in a limited space. Although only one heat introduction member is disposed in the inside chamber in the embodiments, several heat introduction members may be disposed in the inside chamber.

The external heat source is preferably composed of a light source which emits infrared radiation (thermal energy). Although the external heat source is composed of a halogen lamp in the embodiment, it may be composed of a tungsten infrared lamp, glover lamp made of silicon carbide, an electric heater made of nichrome or tantalum, a Nernst glower made of ceramic, or the like. The external heat source may be composed of a heater or the like including W, Mo, V, Pt, Fe, Mn, Ni, Ta, nichrome, kanthal, stainless material, alumel, carbon, graphite, or the like, which can emit infrared radiation upon receiving electricity. Otherwise, the external heat source may be composed of a sheath heater, an IRS type lamp, a radiant tube burner, a carbon arc lamp, a mercury lamp, a xenon lamp, a $CO_2$ laser, or the like.

While the present invention has been shown and described with reference to the foregoing preferred embodiments, it will be apparent to those skilled in the art that changes in form and detail may be made therein without departing from the scope of the invention as defined in the appended claims.

What is claimed is:

1. An air fuel ratio sensor comprising:
   a sensor element having an inside chamber therein;
   an external remote light-emitting, radiant heat source disposed outside the sensor element; and
   a heat introduction member disposed in the inside chamber and connected to the external heat source for introducing heat from the external heat source into the inside chamber.

2. The air fuel ratio sensor of claim 1, wherein the heat introduction member has a first end disposed in the inside chamber and a second end connected to the external heat source.

3. The air fuel ratio sensor of claim 1, wherein:
   the heat introduction member is for introducing the light from the external heat source into the inside chamber as thermal energy.

4. The air fuel ratio sensor of claim 3, wherein the heat introduction member has an optical fiber.

5. The air fuel ratio sensor of claim 1, wherein the heat introduction member has an open end facing a bottom portion of the inside chamber, through which the heat is radiated.

6. The air fuel ratio sensor of claim 1, wherein the external heat source includes at least one selected from a group consisting of a halogen lamp, a tungsten infrared lamp, and a glober lamp made of silicon carbide.

7. The air fuel ration sensor of claim 1, further comprising a temperature detector disposed outside the sensor element and connected to the heat introduction member for detecting a temperature inside the sensor element.

* * * * *